(12) United States Patent
Angelides

(10) Patent No.: US 10,199,126 B2
(45) Date of Patent: *Feb. 5, 2019

(54) SYSTEMS AND METHODS FOR DEVELOPING INDIVIDUALIZED HEALTH IMPROVEMENT PLANS

(71) Applicant: Vivante Health, Inc., Houston, TX (US)

(72) Inventor: Kimon Angelides, Houston, TX (US)

(73) Assignee: Vivante Health, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/892,915

(22) Filed: Feb. 9, 2018

(65) Prior Publication Data

US 2018/0233235 A1 Aug. 16, 2018

Related U.S. Application Data

(63) Continuation-in-part of application No. 15/345,932, filed on Nov. 8, 2016, now Pat. No. 9,928,341.

(60) Provisional application No. 62/457,951, filed on Feb. 12, 2017, provisional application No. 62/254,475, filed on Nov. 12, 2015.

(51) Int. Cl.
*G16H 70/20* (2018.01)
*G06F 17/30* (2006.01)
*G16H 10/60* (2018.01)
*G16H 40/67* (2018.01)

(52) U.S. Cl.
CPC ....... *G16H 70/20* (2018.01); *G06F 17/30864* (2013.01); *G16H 10/60* (2018.01); *G16H 40/67* (2018.01)

(58) Field of Classification Search
CPC ........ G16H 70/20; G16H 40/67; G16H 10/60; G06F 17/30864
See application file for complete search history.

(56) References Cited

U.S. PATENT DOCUMENTS

| | | | |
|---|---|---|---|
| 7,935,307 B2 | 5/2011 | Angelides | |
| 8,066,640 B2 | 11/2011 | Angelides | |
| 8,568,309 B2 | 10/2013 | Angelides | |
| 8,812,244 B2 | 8/2014 | Angelides | |
| 2004/0133080 A1* | 7/2004 | Mazar | A61B 5/0002 600/300 |
| 2008/0299009 A1 | 12/2008 | Angelides | |
| 2009/0264337 A1 | 10/2009 | Angelides | |
| 2010/0191075 A1 | 7/2010 | Angelides | |
| 2012/0029327 A1 | 2/2012 | Angelides | |
| 2012/0231431 A1 | 9/2012 | Angelides | |
| 2013/0035563 A1 | 2/2013 | Angelides | |
| 2013/0078601 A1 | 3/2013 | Angelides | |
| 2013/0187780 A1 | 7/2013 | Angelides | |

(Continued)

*Primary Examiner* — Victoria P Augustine
*Assistant Examiner* — Chad A Newton
(74) *Attorney, Agent, or Firm* — Elizabeth R. Hall & Assocs.; Elizabeth R. Hall

(57) ABSTRACT

Embodiments of the invention include systems and methods for developing individualized health improvement plans including a system for data mining personal health data, structured health related information and unstructured medical narratives and storytelling to identify treatment plans and general techniques that individuals with chronic diseases/symptoms can use to improve their general health and well being.

14 Claims, 11 Drawing Sheets

(56) References Cited

U.S. PATENT DOCUMENTS

| | | |
|---|---|---|
| 2014/0122126 A1* | 5/2014 | Riskin .................... G16H 50/30 705/3 |
| 2014/0154653 A1 | 6/2014 | Angelides |
| 2014/0363794 A1 | 12/2014 | Angelides |
| 2015/0100352 A1 | 4/2015 | Amies et al. |
| 2015/0294073 A1 | 10/2015 | Angelides |
| 2015/0313534 A1 | 11/2015 | Angelides |
| 2015/0317913 A1 | 11/2015 | Angelides |
| 2015/0379199 A1* | 12/2015 | Tambasco, Jr. .......... H04N 5/44 705/3 |
| 2016/0220175 A1* | 8/2016 | Tam .................... A61B 5/1127 |
| 2016/0283563 A1 | 9/2016 | Hodjat et al. |
| 2017/0076630 A1 | 3/2017 | Angelides et al. |
| 2017/0140103 A1 | 5/2017 | Angelides |

\* cited by examiner

FIG. 5

SYSTEMS AND METHODS FOR DEVELOPING INDIVIDUALIZED HEALTH IMPROVEMENT PLANS

CROSS-REFERENCE TO RELATED APPLICATION

The present application claims the benefit of the earlier filing date of provisional application Ser. No. 62/254,475 filed Nov. 12, 2015 and entitled "Systems and Methods for Providing Comprehensive Care for Stoma Patients" and to U.S. Provisional Application 62/457,951 filed Feb. 12, 2017 entitled "Capturing Crowd Wisdom in Individualized Treatment Plans for People with Chronic Diseases". The present application is a continuation-in-part to and claims priority under 35 U.S.C. 120 to U.S. patent application Ser. No. 15/345,932 filed Nov. 8, 2016 and entitled "Systems and Methods for Providing Comprehensive Care for Stoma Patients." Each of these cited applications are hereby incorporated by reference in their entireties.

BACKGROUND OF THE INVENTION

Field of the Invention

This invention is related to systems and methods for developing individualized health improvement plans. More particularly, the invention is related to a system for data mining personal health data, structured health related information and unstructured medical narratives and storytelling to identify treatment plans and general techniques that individuals with chronic diseases/symptoms can use to improve their general health and well being.

Description of the Related Art

Anyone facing a chronic disease or consistent discomfort must typically rely on health care professionals and internet blogs to assess various treatment alternatives. The basic information that is generally available is typically derived from a number of medical records and/or from structured information derived from questionnaires and structured interviews by health care professionals. Such data and information is limited and does not capture the more nuanced responses of individuals.

Thus, there is a need for processes that will capture a more inclusive set of data and related information from unstructured sources.

SUMMARY OF THE INVENTION

Embodiments of the invention include systems and methods for capturing crowd wisdom in developing individualized treatment plans. More particularly, the invention is related to a system for data mining crowd sourced structured health related information and unstructured medical narratives and storytelling to identify treatment plans and general techniques that individuals with chronic diseases/symptoms can use to improve their general health and well being. The crowd wisdom is captured by an information management system that has a processing unit that stores a number of software applications executable by the processing unit. The software applications include a data extraction application that extracts, identifies and links associated processed data from the structured database, the unstructured database and the internet usage database.

One embodiment of the invention is an information management system including: a) a processing unit storing a plurality of software applications executable by the processing unit; b) a structured database; c) an unstructured database including data processed by at least one software application; d) an internet usage database processed by at least one software application for assessing patterns of internet usage; and e) a data extraction application that identifies and links associated processed data from the structured database, the unstructured database and the internet usage database.

Embodiments of the invention include a personalized care management system for providing comprehensive care for individuals with chronic disease or symptoms. The care management system including: a) an information management system for receiving and storing a structured database, an unstructured database, and an internet usage database for an individual participant in the care management system; b) a processing unit, wherein the processing unit comprises computer program instructions for extracting, analyzing and correlating information relevant to a designated health condition of the individual participant from the information management system and an external data source to form a searchable combined information system; and c) a wireless platform in communication with the processing unit and the searchable combined information system, wherein the platform comprises one or more portals, and wherein the platform is configured to maintain an interactive user database for an authorized user of the portal.

Another embodiment of the present invention is a care management system including: a) an information management system for receiving and storing a structured database, an unstructured database, and an internet usage database for an individual participant of a care management system; b) a processing unit storing a plurality of software applications including a data extraction application that identifies and links associated processed data from the structured database, the unstructured database, the internet usage database, and an external data source and a data analysis application that analyzes and correlates the linked information relevant to a designated health condition of the individual participant; and c) a platform in communication with the processing unit and one or more portals, wherein the platform is configured to maintain an interactive participant database accessible by an authorized user of the portal.

Yet another embodiment of the present invention is a method for creating an individualized health improvement plan comprising: (a) creating a structured database, an unstructured database, and an internet usage database for an individual participant in a care management system; (b) extracting information relevant to a designated health condition of the individual participant from the structured database, the unstructured database, the internet usage database and an external data source using software applications residing on a processing unit; (c) converting the extracted information into a searchable combined information system; and (d) communicating the searchable combined information system to an interactive care management platform for analysis and storage. This method may also comprise capturing crowd wisdom by analyzing and correlating the combined information system of the individual participant with related data extracted from numerous combined information systems created for other participants in the care management system.

The foregoing has outlined rather broadly several aspects of the present invention in order that the detailed description of the invention that follows may be better understood.

Additional features and advantages of the invention will be described hereinafter which form the subject of the claims of the invention. It should be appreciated by those skilled in the art that the conception and the specific embodiment disclosed might be readily utilized as a basis for modifying or redesigning the structures and systems for carrying out the same purposes as the invention. It should be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 5 is an exemplary display screen of a user sub-portal of an interactive platform according to an embodiment.

DESCRIPTION OF THE PREFERRED EMBODIMENTS

It is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in any appropriately detailed structure.

Figure 1:
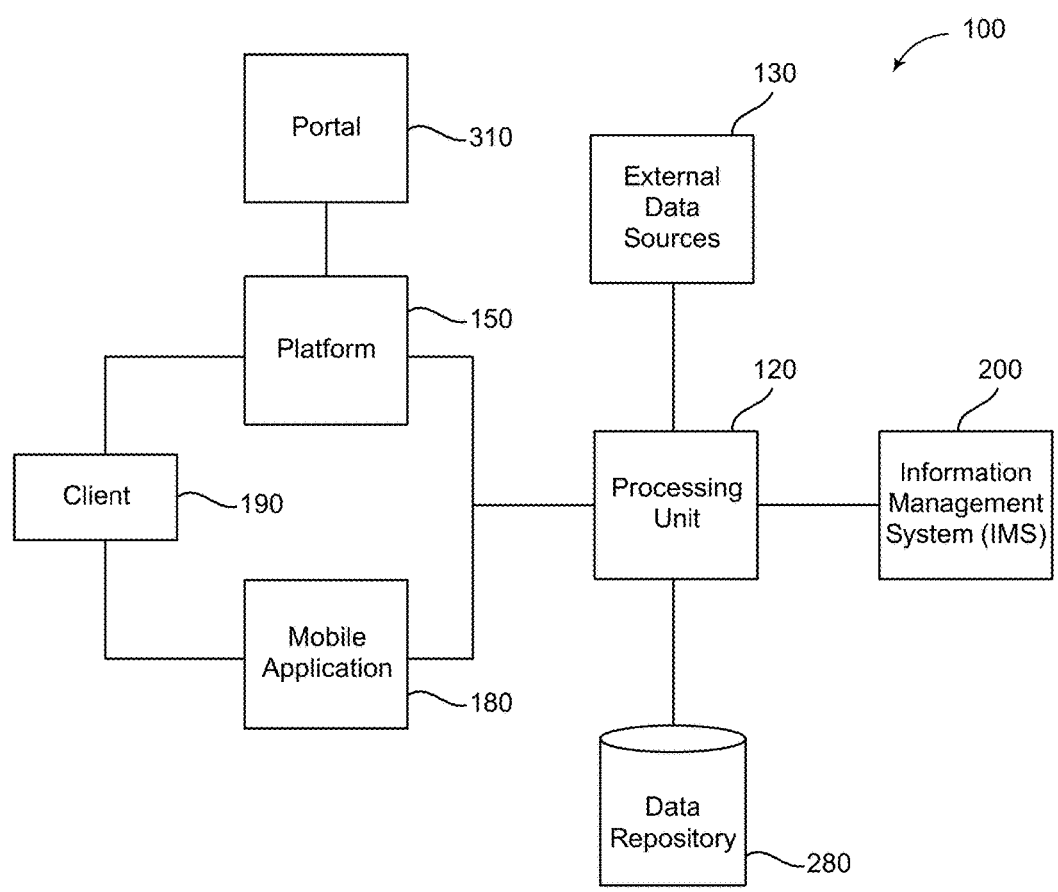
FIG. 1 is an illustration of a system for providing a personalized care management system for a particular participant of the care management system according to an embodiment.
Figure 2:
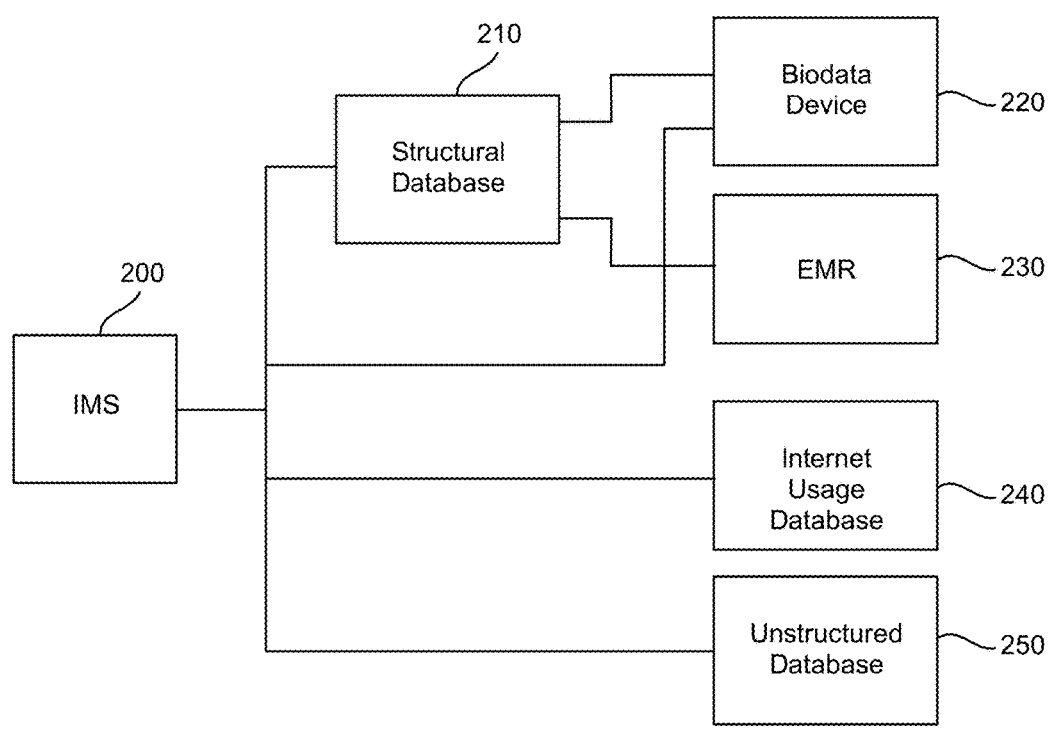
FIG. 2 is an illustration of an information management system of the personalized care management system of FIG. 1 according to an embodiment.

Referring now to the drawings, and initially to FIGS. 1 and 2, it is pointed out that like reference characters designate like or similar parts throughout the drawings. The Figures, or drawings, are not intended to be to scale. For example, purely for the sake of greater clarity in the drawings, component size and spacing are not dimensioned as they actually exist in the assembled embodiment.

Embodiments of the invention include systems and methods for capturing relevant data from a personalized information system in developing individualized health improvement or treatment plans. More particularly, the invention is related to a system for data mining structured health related information and unstructured medical narratives and storytelling to identify treatment plans and general techniques that individuals with chronic diseases/symptoms can use to improve their general health and well being.

Personalized Care Management System for Persons with Chronic Disease

Embodiments of the invention include systems and methods for providing personalized care management for persons with chronic disease. One embodiment of the care management system includes an information management system for extracting related information from multiple data sources and communicating that information to a web portal or platform configured to periodically provide an individual system participant/client with reminders, advice and coaching.

FIG. 1 schematically illustrates an embodiment of a care management system 100 for providing personalized health improvement plans for individual participants or clients. The system 100 includes: an information management system 200 (IMS), a processing unit 120, a platform 150, a database repository 280, a web portal 310, and a mobile application 180. The information on the web portal/platform is accessible by the client 190 of the care management system and other authorized users through a set of sub-portals or data access modules.

Information Management System

FIGS. 1-2 show one embodiment of the information management system 200. In this embodiment, information extracted from various data sources is transmitted to a processing unit 120 and stored on a data repository 280. Data from structured data sources 210, from unstructured data sources 230, and/or from internet usage data sources 240 is extracted, analyzed, and correlated by software applications executable by the processing unit 120.

The processing unit 120 has a number of software data extraction and data mining applications, including a plurality of inference engines and algorithms. Data related to a client's health condition is extracted from structured data sources, unstructured data sources, internet usage data sources, and/or external data sources. The extracted information is linked, analyzed, and correlated by software applications executable by the processing unit 120. These software applications identify, associate, and correlate the relevant information in each data source and link the relevant information identified in each data source to build a searchable combined information system that is communicated to a platform 150 and the data repository.

The combined information system on the platform 150 is searchable and downloadable by a client or authorized user through a mobile device such as a smart phone or through a computer. Typically, a software application available for download through app stores or distribution platforms will instruct and configure interactive communication between the combined information system and a smart phone, a tablet computer, or any other programmable computing unit.

Structured Data Sources.

Structured data is defined as data that is numerically based. Structured data is easily processed by data extraction and analytic programs residing on the processing unit 120.

Typical examples of such data include electronic medical records (EMR) and data generated by biodata devices.

Electronic medical records capture structured data from a number of sources such as a person's medical history, laboratory data, diagnoses, treatment plans, insurance codes, and their family's medical history. The EMR of an individual contains initially numerically based data, such as clinical chemistry data, and data that is not directly entered as numerical data, such as x-rays or MRIs, that are typically captured in the EMR using structured formats for translating color or light absorption into numerical data that is easily processed. Other medically related data that is numerically captured include data captured from a predetermined selection of boxes or statements on drop down menus that are selected by health related professionals. The EMR data 230 is collected and stored in the structural database 210.

Another example of structured data is data that is measured by one or more biodata devices 220. Biodata devices 220 typically collect physical information or measurements of an individual user. The biodata devices 220 are often equipped with the necessary software to process the data generated by the device into numerically based structured data and to communicate the collected structured data to the structural database and the processing unit 120. Such biodata devices 220 commonly include software applications that are formatted to collect, process, and transmit numerically based data to designated devices having a processor, such as the processing unit 120, or to a mobile device in communication with the individual.

The structured data 210 is gathered and generally subjected to data extraction analytic programs residing within the IMS 200 and/or the processing unit 120. Typically, the data extraction programs employed for the structured data identifies and maps key data elements, links related data, plots data over time and stores the data in a structural database.

Unstructured Data Sources.

descriptions of a patient's symptoms, general well being, and perceived effectiveness of treatment plans. Currently, medical records contain all subjective notes in a textual format. Since unstructured data is more difficult to analyze, it is not currently processed by data extraction programs and incorporated into the health treatment decision-making process.

Significant insights into a person's health can be gained by analyzing aspects of their home life, their medical narratives, their stories, and generally how they operate on a daily basis. The types of insights gained by understanding a person's social structure, daily routines and cultural background is important in understanding and personalizing that person's experience and how that person copes with a chronic condition on a daily basis. This type of unstructured data is vital to finding personalized treatment plans that a person will adhere to and that will provide positive changes in a person's quality of life.

Although people share the same disease or the same chronic symptomology, their ability to navigate through the symptoms often will include personal adjustments to their daily routines. Many people facing chronic diseases and associated uncomfortable or embarrassing symptoms will try alternative approaches that they are unwilling to share with their physicians. Thus, a great deal of relevant information does not appear in their medical records or in any of the structured data used to map treatment plans and their success. Often these alternative approaches will include herbal remedies, supplements, acupuncture or acupressure, reflexology, relaxation techniques, or exercise regimes such as yoga or stretching.

Unstructured data often includes a daily logging of a participant's daily symptoms, general well being, habits and routines in a textual format. In one embodiment of the information management system 200, the unstructured data 230 will include crowd wisdom captured by including an analysis of thousands of daily logs of thousands of the care management system participants. The collective wisdom of thousands of users captured within these daily medical narratives and personal experiences will be processed using various algorithmic based data extraction applications. Capturing crowd wisdom on numerous variations in health treatments (such as the role of diet, exercise, and/or alternative health approaches) on the general well being of participants with common symptomology and chronic conditions will benefit all participants.

Common themes of symptoms, daily routines, and treatments plans (medically recommended and user determined alternative health treatments) will be extracted and correlated using a variety of analytic engines such as natural language processing, inference engines, and by following Markov patterns. information from the medical narratives, match and compare the information extracted from thousands of persons and assess similarities and differences. The similarities and differences will be collated and analyzed to extract relevant information.

The analyzed and collated unstructured data is gathered and generally subjected to data extraction and analytic programs residing within the IMS 200 and/or the processing unit 120. Typically, the data extraction programs employed for the unstructured data identifies and maps patterns, common health treatments, alternative health treatments, and general wellness data. The unstructured data is collected in the unstructured database 230 and sent to the processing unit for further analysis.

Internet Usage Data Sources.

Internet usage data is defined herein as the client's, as well as other system participants', internet usage patterns. The internet usage patterns of system participants will be assessed for the information that the system participants with common health conditions are searching on the internet to derive their use patterns, what sites they are searching, their personalized likes and dislikes, their internet inquiries, and their downloaded information. For example, users may search for information on certain drugs/supplements, people with the same disease or similar symptoms, or new treatment plans. Information will also be derived from the sequence of user searches and the temporal associations of their searches by mapping the transition and time between searches.

The information derived from analyzing system participants internet searches and the blogs that they read and contribute to will be correlated with the daily medical narratives of users with similar diseases or symptomology to enhance the data input to be processed by the processing unit. For example, a system participant's "search" pages can be considered in personalizing their profile as reflecting their inner consciousness. In addition, the temporal associations of their search can assist in mapping patterns and probabilities of symptom recurrences and the temporal relationship of such recurrences.

External Data Sources.

External data sources are defined herein as data sources that are not maintained or controlled by the care management system's administrator. The internet will be routinely searched by the care management system's professionals for information from numerous blogs and other sites containing information related to the health and wellness of people with certain diseases and/or symptomology as well as laboratory or clinical sites, insurance companies, media companies, call centers, care providers, account administrators, durable medical equipment (DME) suppliers, and other sources.

Processing Unit

The processing unit 120 stores a number of software applications executable by the processing unit. The software applications include a data extraction and analysis application that extracts, identifies and links associated processed data from the structured database 210, the unstructured database 230 and the internet usage database 240. The data extraction and analytic applications data mine the structured health related information, unstructured medical narratives such as storytelling, internet usage data as well as external data sources to identify treatment plans and general techniques that individuals with chronic diseases/symptoms can use to improve their general health and well being.

The data extraction applications include inference engines and other algorithmically based applications that it uses to identify and associate relevant information in each data source and to correlate and link the relevant information identified in each data source to build a searchable combined information system that is communicated to a platform 150 and stored in the data repository 280. The combined information system on the platform 150 is searchable and downloadable by authorized users of the care management system through a mobile device such as a smart phone or through a computer.

In one embodiment, the processing unit 120 can include a multitude of interrelated elements. Embodiments of the processing unit can be implemented to some extent as software modules installed and running on one or more processing systems, such as servers, workstations, tablet computers, PCs, and so on. The processing unit 120 may include at least one computer processor as well as a knowledge module. An application program interface (API) is code that allows two software programs to communicate with each other. The API defines the correct way for a developer to write a program that requests services from an operating system (OS) or other application. A suitable interface can be used to edit the knowledge module; for this purpose, the interface exposes a set of APIs in corresponding libraries. These APIs allow submitting commands for adding, removing, or updating of data in the knowledge module 280.

The knowledge module differs from a standard database since in this case further knowledge or informational data may be derived from existing knowledge using inference, analysis, crowd sourced wisdom and continual monitoring data from the client. Thus, the knowledge module is a data repository and a "care" analysis engine. The knowledge module can include a database or a data repository for the formatted measurement data. As shown, the knowledge module can also receive data from an external data sourced database 1300. The external sourced database may include data from various sources, such as laboratories, insurance companies, hospitals/clinics, media companies, 24/7 call centers/caregivers, account administrators, and other sources. The data from the external database can be extracted and transferred to the knowledge module using dynamic APIs.

The processing unit 120 processes information from the information management system 200 and one or more external data sources 280 to determine personalized clinical and nutritional decision analytics for clients or individual system participants. The external data sources can include a laboratory, insurance companies, media companies, call centers, care providers, account administrators, durable medical equipment (DME) suppliers, and other sources. The external data sources may also include information from numerous blogs and other sites containing information related to the health and wellness of people with certain diseases and/or symptomology.

The processing unit 120 may include one or more algorithms that provide both content and personalized rules to provide feedback to the user in real time. For example, the processing unit 120 may include code for predicting trends based upon the client's 190 personalized health profile and preferences. The information and analyses may be stored in a data repository 280.

The processing unit 120 can represent one or more general-purpose processing devices such as a microprocessor, central processing unit, or the like. More particularly, the processor may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also be one or more special-purpose processing devices such as an application specific integrated circuit (ASIC), a field programmable gate array (FPGA), a digital signal processor (DSP), network processor, or the like. The processor can be configured to execute instructions for performing the operations and steps discussed herein.

The processing unit 120 can also include a computer readable storage medium on which is stored an appropriate operating system (not shown). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. One or more sets of instructions (e.g., software) embodying any one or more of the methodologies or functions described herein may also be stored on the computer-readable medium. The instructions may further be transmitted or received over a network.

Instructions or program code embodied on the computer readable medium may be transmitted using any appropriate medium, including but not limited to wireless, wireline, optical fiber cable, RF, etc., or any suitable combination of the foregoing. Computer program code for carrying out operations of the present invention may be written in an object oriented programming language such as Java, Smalltalk, C++ or the like. However, the computer program code for carrying out operations of the present invention may also be written in conventional procedural programming languages, such as the "C" programming language or similar programming languages. The memory may include both volatile random access memory (RAM) and some form or forms of non-volatile computer memory such as a hard disk drive, an optical disk drive, or an electrically erasable programmable read-only memory space (also known as EEPROM or Flash memory). The memory can be connected to the processor and to other system components.

The processing unit 120 processes information from the information management system 200 and one or more external data sources 130 to determine personalized clinical and nutritional decision analytics for individual system users 190. The processing unit 120 may include one or more algorithms that provide both content and personalized rules to provide feedback to the user in real time.

The processing unit 120 communicates all the analyzed data and searchable combined information system to a data repository 280 for storage. The data repository 280 stores a database comprising a specific client's related data, as well as relevant data from all of the health management system participants and external data sources. The data repository 280 can be a local storage unit or a remote storage unit. The data repository may be a magnetic storage unit, optical storage unit, solid state storage unit or similar storage unit. The database can be a monolithic device or a distributed set of devices.

Interactive Web Platform for Care Management System

A computerized platform 150 communicates with the processing unit 120, database repository 280, web-based portal 310, mobile applications 180 and authorized users of the care management system. By way of example and not limitation, a care management software application running on a mobile device periodically receives real-time information and suggestions via a user sub-portal. Such information and suggestions have been analyzed from the relevant data received by the platform from the processing unit and the data repository.

Figure 3:
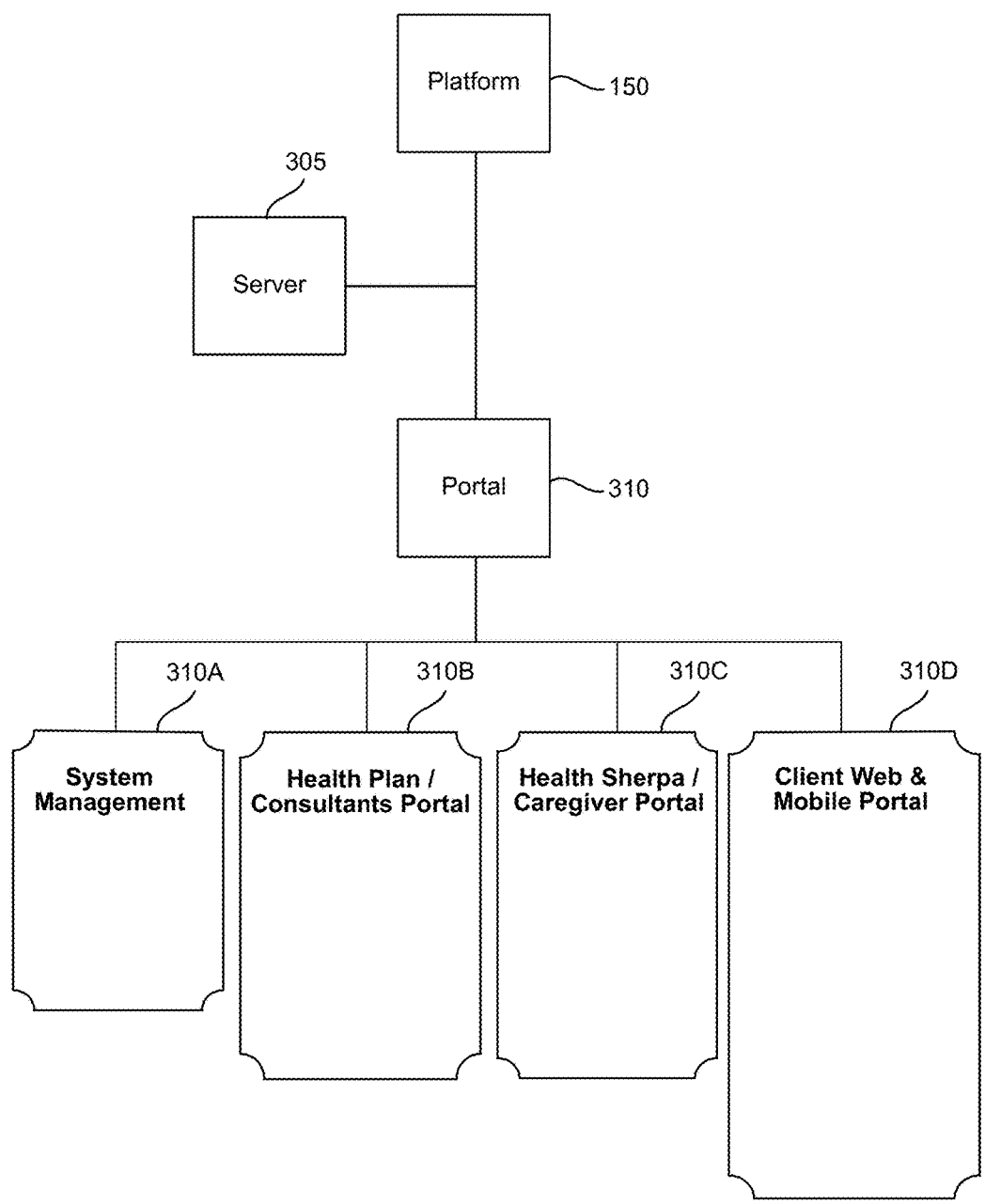
FIG. 3 is an illustration of a platform and a portal with its sub-portals that communicate with the platform of the personalized care management system of FIG. 1 according to an embodiment.

FIGS. 1 and 3 illustrate an interactive platform for personalized care management according to an embodiment of the present disclosure. The platform may have a secure server 305 and a web portal 310. The portal 310 provides one or more interfaces for reporting and displaying the data from the platform to the authorized system users as well as support personnel via various sub-portals, each sub-portal having restricted access.

The platform 150 can include a multitude of interrelated elements. Embodiments of the platform 150 can be implemented to some extent as software modules installed and running on one or more processing systems/computers, such as servers, workstations, tablet computers, PCs, personal digital assistants (PDAs), smart phones, and so on. The processing systems may include at least one computer processor as well as a memory (not shown). The platform may also include a special interface device that can accommodate a number of different wireless and hard wired devices similar to a "switch" box. The platform processor may be the same or similar to that of the processing unit 120 and may include a knowledge module like that of the processing unit.

The platform processor can represent one or more general-purpose processing devices such as a microprocessor, central processing unit, or the like. The platform processor can be configured to execute instructions for performing the operations and steps discussed herein and can include a computer readable storage medium on which is stored an appropriate operating system (not shown). One or more sets of instructions (e.g., software) embodying any one or more of the methodologies or functions described herein may also be stored on the computer-readable medium. The instructions may be transmitted or received over a network using any appropriate medium, including but not limited to wireless, wireline, optical fiber cable, RF, etc., or any suitable combination of the foregoing.

The platform 150 may also include one or more input/output network interface device (not shown) for implementing user-oriented input/output through software drivers and hardware for controlling output to input/output devices such as mobile devices through a network. The platform 150 can be accessible to any number of other devices, user machines and users through a network. The other devices can be mobile phones, desktop computers, laptop computers, hand-held computers or similar computing device. The network can be local area network (LAN), such as an intranet within a company, a wide area network (WAN), such as the Internet or similar communication system. The network can include any number of networking and computing devices including any number of wired and wireless devices. The network may include connections, such as wire, wireless communication links, or fiber optic cables.

The platform 150 is in communication with the data repository 280 and the processing unit 120. The data repository includes a database comprising a specific client's data and related data from other system participants, as well as external data sources. The platform processor may include software applications with instructions to implement one or more rules. For example, the rules may pertain to a daily meal or activity plan for the client 190, a matching of the client to a coach or health guide (a Health Sherpa®), nutrition guidance, client reports and predictions, client health profiles and video/chat sessions.

Typically, the platform processor will include code for predicting trends based upon the individual client's 190 personalized health profile and preferences. For example, the rules may pertain to a daily meal or activity plan for the participant 190 based on personal preferences, a matching of the client to one or more health consultants, nutrition guidance, exercise routines, general health predictions and alerts, trends and improvements in the client's health profile and video/chat sessions. Various parameters are considered in determining recommendations, educational messages, and directives to the client. The platform processor then analyzes and correlates the relevant data to determine useful information for the specific client and transmits that information to the client, including information relating to nutrition, exercise advice and treatment decisions.

In one or more embodiments, the platform 150 can facilitate the interaction between a client, a caregiver, a counselor, a financial/claims administrator and any other authorized user using a designated web-based portal 310 or multiple sub-portals 310A-310D. Access to the platform 150 may be controlled by a system administrator of the care management system 100. Only users with authorized credentials may be allowed access to the platform 150 through a specific sub-portal. For example, the memory may include cloud storage that stores profiles for one or more persons that define at least one of access privileges or preferences for respective system users. Access privileges may also be driven by a set of interactive rules based on health care privacy rules and/or clinical pathways.

The portal 310 is typically web-based. The portal 310 receives analyzed data content from the processing unit 120. The portal 310 provides one or more interfaces for reporting and displaying the data from the platform. The portal 310 can be used to create and display profiles of individual clients/users. The portal 310 can be used to display information on an individual client's symptomology, treatment progress, medications, nutritional status, etc. Portal access is controlled by the system administrator through established access privileges. As illustrated in FIG. 3, the portal 310 may include a number of modules or sub-portals with access specifically designated to authorized users. The portal or sub-portals can communicate with authorized users through mobile devices.

The portal 310 may include a plurality of sub-portals such as, without limitation, a System Management Portal 310A, a Health Plan/Consultant's Portal 310B, a Health Sherpa/Caregiver Portal 310C and a Client Portal 310D. The portal 310 is configured to add contextual metadata to at least a subset of the analyzed data communicated to the platform. The contextual metadata can include one or more metatags that identifies an origin of the subset of analyzed data within the one or more sub-portals. The contextual metadata further comprises at least one of a unique identifier associated with access privileges for a particular sub-portal.

The System Management Portal 310A may be configured to receive data from the platform that is relevant to financial claims and system management. For example, the System Management Portal 310A may include aggregate HIPAA information, compliance reports, performance dashboard, client membership data and other related information.

The Health Plan/Consultant's Portal 310B may be configured to receive data from the platform that is relevant to a health plan manager/consultant. For example, the Health Plan/Consultant's Portal 310B may include personal health records, insurance related records, financial administration records, performance metrics, treatment plan options, crowd sourced data related to certain chronic conditions or symptoms and other related information.

The Health Sherpa/Caregiver Portal 310C may be configured to receive data from the platform that is relevant to a counselor/caregiver of a client with chronic health concerns. For example, the Health Sherpa/Caregiver Portal 310C may include clinical summaries, electronic medical records, prescription information, lab records, personal health records, general health and wellness blogs, clinical notes, clinical alerts, information on health coaching and previous coaching sessions with the person, assessment tools, intervention tools and other related tools and data. The Health Sherpa/Caregiver Portal 310C may also have access to crowd sourced data related to certain chronic conditions or symptoms, symptom predictions, as well as the client's personal preferences and preferred treatment options.

Figure 4:
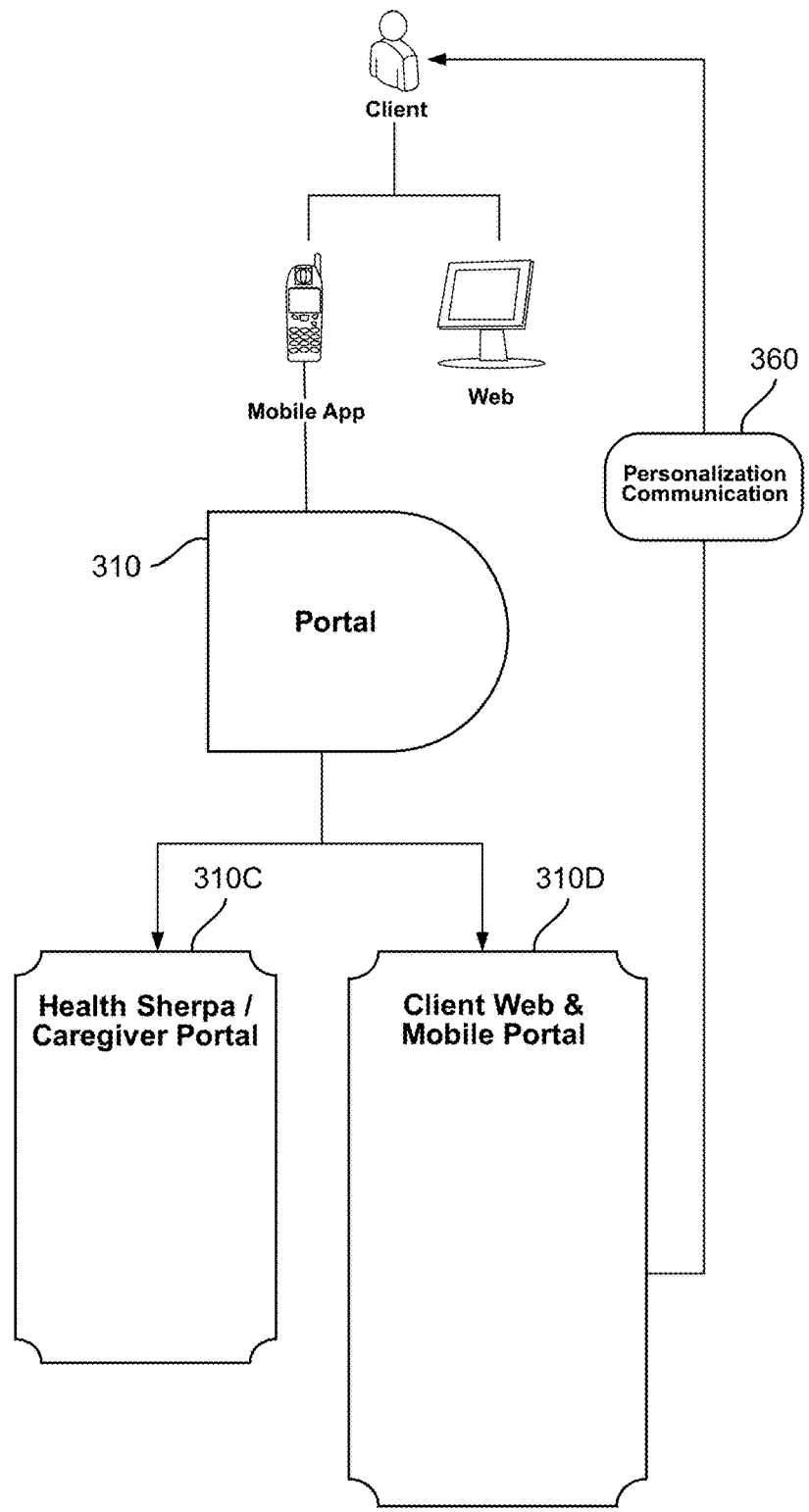
FIG. 4 is an illustration of a communication system between the client, the client sub-portal and other parts of the personalized care management system of FIG. 1 according to an embodiment.

The Client Portal 310D may be configured to receive data from the platform that is beneficial to a specific client/participant of the care management system. The Client Portal 310D (and any of the other portals 310A-C) is an interactive portal and it may be accessible from the Internet or as a mobile software application as shown in FIG. 4. The Client Portal 310D is configured to receive a plurality of information from the client and the information management system on a periodic basis. The Client Portal 310D is further configured to provide information on daily diet and exercise plans, informational videos and on-demand or scheduled chat sessions with the Health Sherpa and caregiver team, education and feedback, personalized lifestyle and behavioral resources, progress status to goals and other related information.

Advantageously, the Client Portal 310D is configured to provide alerts and reminders. These can be transmitted to the client's mobile device or on another computing device and may be presented via application software. Alternatively, the information may be contained in text messages, electronic mail messages or other general-purpose application software resident on the mobile/computing device. The Client Portal 310D is also configured to provide real-time interventions using a personalized user profile for the user.

Figure 5:
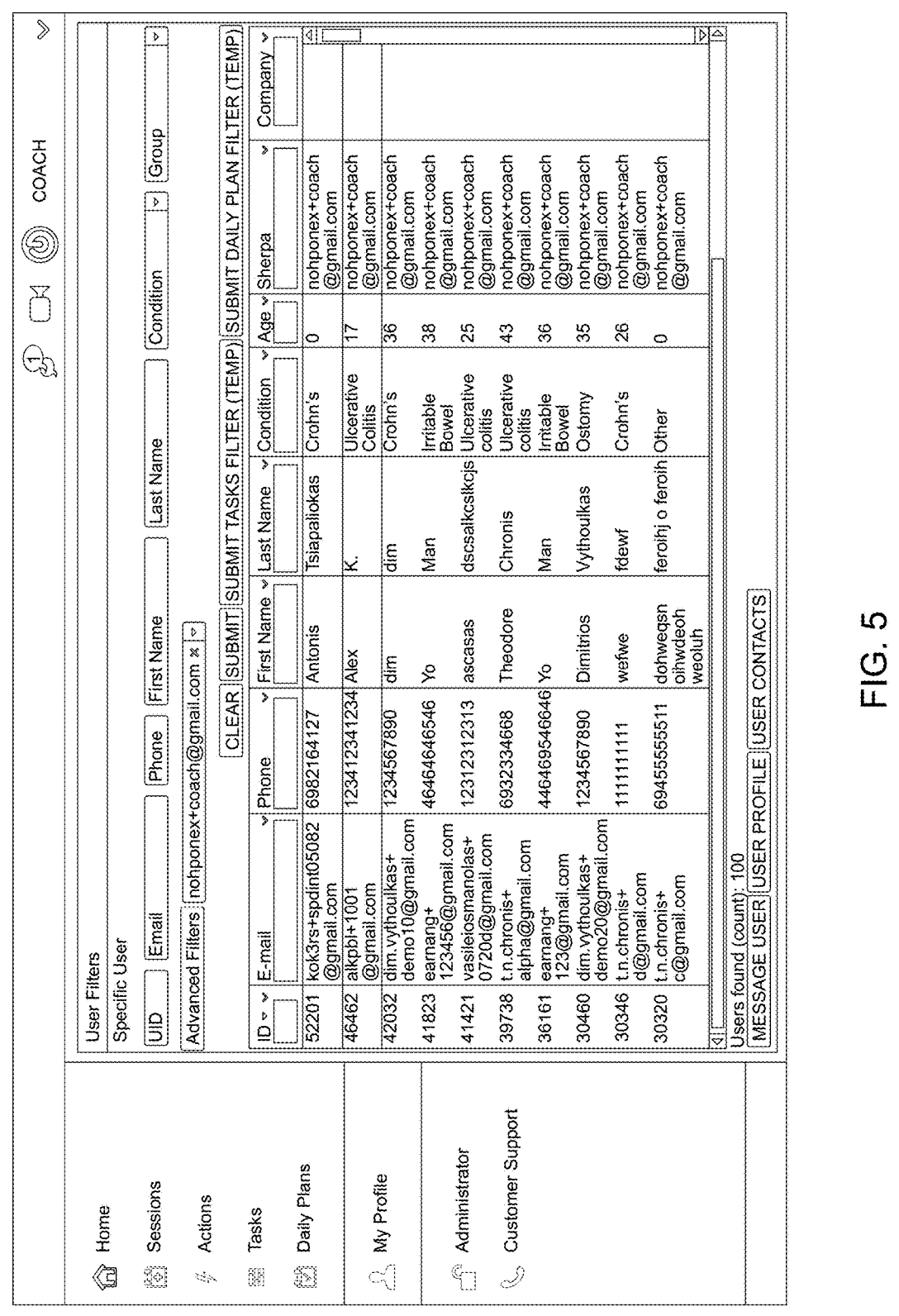

An exemplary interactive screen, such as the one shown in FIG. 5, may be used to enter information for identifying a client, such as email, user id, phone, first and last names, medical condition, age, company name into the portal 310. A designated Health Sherpa®, a team of advisers and/or a caregiver may be matched with each client. Information on the Sherpa may also be entered in the portal 310. Additional information such as the client's weight, height, daily diet and exercise plans, daily tasks, daily or weekly health status, stress levels, etc. may also be entered in the processing unit, the data repository and/or the platform. The portal 310 can be configured to allow the user (for example, the Sherpa) to message the client, retrieve the client profile and contacts, etc. The portal 310 may use an email authentication method, for patient authentication. Other authentication methods, such as authentication of the mobile device, are also applicable.

The specific client 190 or user of the care management system 100 may view his/her data and communications on a mobile device. In one embodiment, the portal 310 may be accessed from the same mobile device that is configured to run a biodata device software application, such as an ostomy bag monitor, a glucometer, an analyte sensor and/or an activity software application.

Figure 6:
FIG. 6 is an exemplary display screen of a healthcare counselor sub-portal of an interactive platform according to an embodiment.

The Client Portal 310D can be configured to facilitate a real-time messaging or chat session between the client and the Health Sherpa® or caregiver. The Client Portal 310D is configured to allow the client to schedule a chat session, determine the time of his/her next scheduled session and to access previous coaching sessions. The Health Sherpa/Caregiver Portal may be configured to allow the Health Sherpa designated to a specific client to determine the number of sessions in queue and to access predetermined information from previous coaching sessions with the client. An exemplary display is shown in FIG. 6.

A high-security firewall (not shown) is used to provide a secure communication channel between the platform 150 and each sub-portal and any mobile applications. The system client and/or authorized users are required to authenticate themselves via an authentication layer.

The Client Portal 310D can be used to track client's preferences, especially those relating to diet and exercise. The tracking of favorites and the updating, analyses and recommendations based on a user's favorites is normally a data-intensive function. The tracking and updating of the client's favorites is generally based on information either gathered from the user at an interview, log entries, or from responses to general questionnaires. Accordingly, the tracking, updating, analyses and recommendations based on favorites are normally performed by the processing unit and/or the platform, following transmission of real-time client updates from the client's mobile device or biodata device. Thus, the constant review and analysis of an individual's general health and symptomology allows the system to personalize all treatment regimes and recommendations.

For example, the recommendations for eating can be highly specific and personalized (e.g., eat X calories of carbohydrates selected from "your favorites" mashed potatoes and pinto beans; eat X calories of lean protein, selected from "your favorites" shrimp and egg whites). Similarly, recommendations for exercise can include recommendations for exercise duration and exertion level. Exercises may also be personalized for stretching particular muscles or as selected by a physical therapist to assist persons with chronic back pain or poor knee/hip mobility.

Furthermore, messages can be sent based on suspected allergies or intolerances such as bronchial allergies to volatile compounds such as perfumes, contact allergies to soap additives or textiles, food allergies to certain foods such as shrimp or berries, or food intolerances such as milk products for lactose intolerant individuals or gluten products for colitis. Or, the client/user can be directed to stop eating after a certain time or the client may be directed to stop or start exercising based on heart rate.

The platform 150 and its ability to communicate with mobile devices and various computers or processors provides both short and long term benefits. The short term advantages of this platform may include real-time alerts or real-time feedback that includes dietary and nutritional information and liquid intake to help regulate every day health; reference to certain advantages or risks seen for certain health treatments or therapies on symptomology; aid in meeting nutrition requirements and the absorption of foodstuffs; and the enablement of individual reporting and monitoring of general health and a person's likes and dislikes.

The care management system can also be used in medical situations such as emergency rooms, intensive care units, assisted living centers or rehabilitation centers. In institutional use the client is the institution and the platform 150 can facilitate remote tracking by health care professionals of one or more system users or patients by allowing hospitalized patients and nursing staff to automatically alert the nursing station that a patient is in trouble or in need of help. The constant monitoring that tracks biodata devices 220 (including hospital monitors, medications, and infusions) of multiple patients can help with the care and management of hospitalized patients. This can reduce the reliance on nursing staff and avoid costly mistakes. Furthermore, this can provide physicians with concrete evidence of patient treatment responses and general health before release. Additionally, it may reduce a length of stay in the hospital for certain patients with more real time data and nutritional counseling prior to discharge.

Using the Personalized Care Management System

Setting Up the System.

Once a client, member, or individualized user 190 enrolls to use the care management system, the client must selectively approve the entry of data and information to be analyzed by the health care management system 100. Often this will include the use of personal data such as clinical records, as well as client entered data such as daily health logs.

According to an embodiment of the care management system, a client specific Information Management System (IMS) is established including a Searchable Combined Information System (SCIS). The system administrator will set up the client IMS system having a client SCIS that includes data that has been extracted, data mined, analyzed and correlated from a structured database 210, a participants internet usage database 240, an unstructured database 230 of client and other system participants information, and an external data source database 130 by software applications executed by the processing unit 120.

The Searchable Combined Information System (SCIS) is communicated to the platform 150 and the data repository 280. Client approved system users are given restricted access to the SCIS through a web portal 310. The system administrator creates a plurality of sub-portals, each sub-portal allowing access to only a subset of data and information and is accessible only to specific client approved users. The system administrator creates and manages the sub-portal access privileges.

The care management system may offer personalized health treatment plans, advice and recommendations to specific clients. This personalization of the care management system may be facilitated by a group of health care professionals and counselors (herein referred to as the health care group or caregivers and/or Health Sherpa®) identified by the care management system professionals as being particularly qualified to assist the client 190 according to the client's general health and any chronic disease or symptomology experienced by that client. The identified Health Care Group and/or Health Sherpa may be assigned to that client to assist the client in developing health treatment plans, exercise plans, nutritional plans and to answer the client's questions.

The Health Sherpa/Caregiver Portal 310C may be configured to receive relevant data from the SCIS to allow the assigned Health Care Group or Caregiver to assist the client. For example, the Health Sherpa/Caregiver Portal 310C may include clinical summaries, electronic medical records, prescription information, lab records, personal health records, clinical notes, clinical alerts, information on health coaching and previous coaching sessions with the patient, assessment tools, intervention tools and other related tools and data. The Health Sherpa/Caregiver Portal 310C may also be configured to allow any one of the Health Care Team to set up a live chat or conference with the client to provide more personalized service.

The Client Portal 310D may be configured to be an interactive sub-portal to receive data from the SCIS or to communicate with any one of the other sub-portals, especially the Health Sherpa/Caregiver Portal 310C. The Client Portal 310D is configured to receive a plurality of information from the client on a periodic basis. For example, the user can input how s/he feels on a daily basis. The Client Portal 310D is further configured to provide information on daily diet and exercise plans, on-demand and scheduled videos and chat sessions with the Health Sherpa and caregiver team, education and feedback, personalized lifestyle and behavioral resources, progress status to goals and other related information.

Advantageously, the Client Portal 310D is configured to provide alerts and reminders. These can be transmitted to the client's mobile device 180 or on another computing device and may be presented via application software. Alternatively, the information may be contained in text messages, electronic mail messages or other general-purpose application software resident on the mobile/computing device. The Client Portal 310D is also configured to provide real-time interventions using a personalized user profile for the client.

In another aspect, the Client Portal 310D provides the client with uniquely tailored advice and recommendations, particularly on diet and exercise, based on client preferences. The advice and recommendations are continually updated and further refined as new information on preferences is added by the client. The individual tailoring of recommendations and advice is performed in view of the user's preferences, limitations and individualized risk assessment as continually updated. The care management system may include algorithms that can sort through client preferences for diet and exercise preferences to provide uniquely tailored advice, recommendations and education for the client. The number of selections by the algorithm quickly increases as the client continues to provide feedback, leaving a set of instructions which is so detailed as to essentially be a unique code for the client. Thus, the care management system typically involves progressively personalizing the system for each client using a Progressive User Personalization process.

Because no two individuals are alike, the Progressive User Personalization starts with the individual (not a group) and creates a personalized experience for the client, an experience that continually builds on experiential use of the system and input into the database. Profiles are created, risks are stratified, program results are tracked and measured, interventions are designed based on the experience, and as the individual's database becomes more personalized and tailored to fit their needs and lifestyle, and personalized communication 360 with the client delivers content, tips, messages, and relevant information to exploit the "teachable moment" to lead to long-lasting behavior change.

The personalized communications 360 are not static but are interactive and expressly tailored to an individual's needs. The personalized communications give the client rich content to engage them in managing their own health, and provides the connectivity and coordination that individuals need to navigate within healthcare systems and treatments. The technology combines the key elements of simplicity, accessibility and convenience, engagement and community, and tracking and measuring to effect meaningful interventions. The Progressive User Personalization process is embedded into the program to provide constant virtual health and wellness coaches.

Coordinating the Care Management System with a Biodata Device.

One embodiment of a personalized care management system includes data input from a biodata device 220. Biodata devices may include without limitation a glucometer, an ostomy bag monitor, a temperature sensor, a heart rate monitor, an EKG or EEG device, a blood pressure monitor, an analyte sensor or an activity sensor. A specific example of coordinating the care management system with a biodata device is given below for the incorporation of an ostomy bag monitor as described in detail in U.S. patent application Ser. No. 15/345,932 filed Dec. 5, 2017 and entitled "Systems and Methods for Providing Comprehensive Care for Stoma Patients" the entirety of which is hereby incorporated by reference herein.

Example of Care Management System with Ostomy Bag Monitor

An ostomy is a surgical procedure used to create a small opening or stoma on the abdominal wall for releasing waste matter from the bowel or bladder. A stoma appears like a small spout. Waste matter that comes out of the stoma is collected in an external ostomy bag. An ostomy bag allows the stoma to drain into a sealed collection bag while protecting the surrounding skin from contamination. Thus the ostomy bag is typically a water-tight flexible elastomeric bag that attaches directly to the stoma.

Figure 7A:
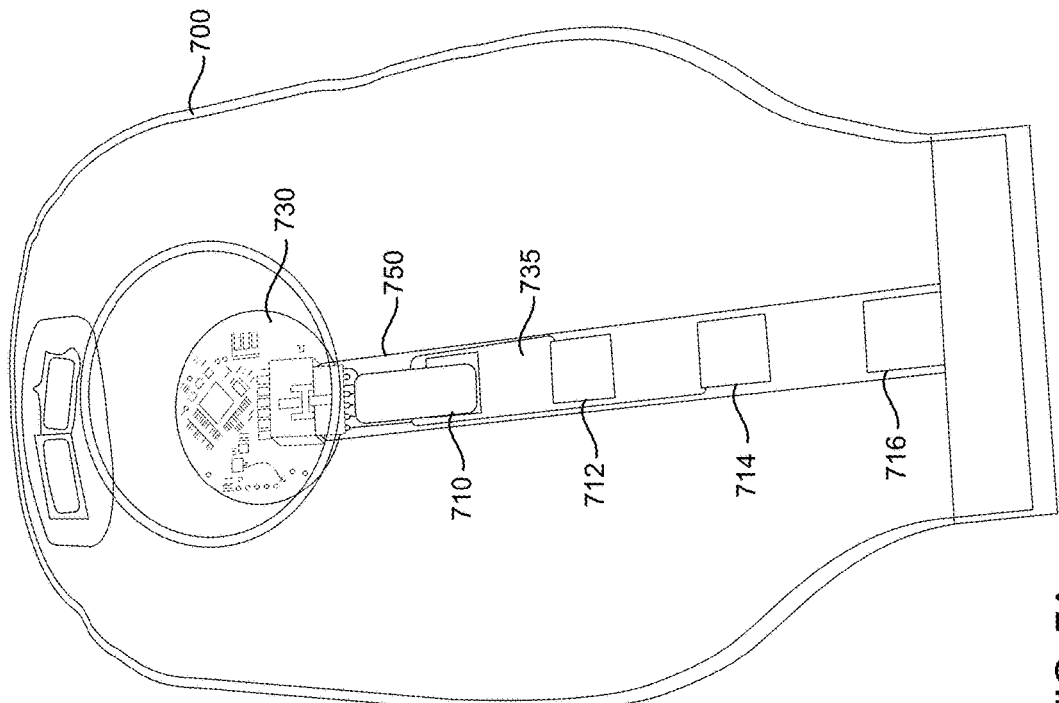
FIG. 7A is a schematic side view of an embodiment of a sensor device mounted on an ostomy bag with a schematic illustration of a mobile application configured to detect a fluid measurement in an ostomy bag.
Figure 7A:
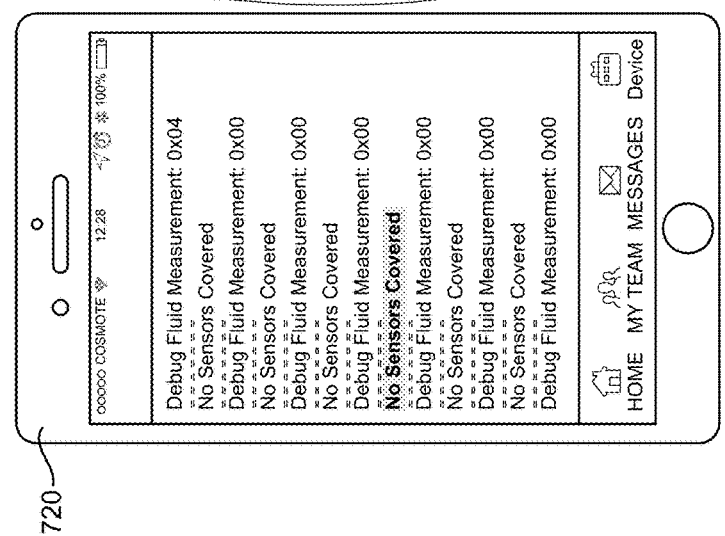

One embodiment of an ostomy bag monitor is illustrated in FIG. 7A. FIG. 7A shows an ostomy bag 700 with one or more sensors 710 configured to detect a parameter of the contents of the bag, such as the level of fluid in the bag, and to communicate the measured parameter to a mobile application 720.

Parameter Sensors.

Sensors 710 may include sensors that measure more than one parameter of the bag contents or they may measure the same parameter. The parameter sensors 710,712,714,716 are in communication with one or more communicators 730. Thus, a collection bag can be customized by a patient, a health care provider or a researcher to measure, store, calculate, communicate, record and/or track one or more desired parameters.

The parameter sensor(s) are mounted on the ostomy bag by a mounting device 735. The mounting device 735 may be removably mounted on the ostomy bag. For example, the parameter sensor may be removably attached to the outside of an ostomy bag via a mounting strip Velcro type attachment strips, or a covering with an adhesive side having one or more parameter sensor (a Band-Aid type of attachment with one or more parameter sensors substituted for the gauze patch), or insertion into a pouch on the outside of the bag. The sensor device can be attached horizontally, vertically or diagonally across one section of the bag. The parameter sensors may be mounted in any desired position for monitoring as long as the parameter sensors are in communication with the measurement communicator 730.

Although the description continues with references to "a" (single) sensor device, it should be understood that different sensor devices and different parameter sensors may be employed to provide and communicate different sensed parameters. A non-exhaustive list of different example types of parameter sensors may be employed for measuring the following:

Volume:

a) Flex/bend and stretch sensors contained within an adhesive strip can detect changes in resistance, as the flex and stretch sensors bend or are extended the electrical resistance changes and is recorded by the measurement communicator; b) Pressure sensors can measure the pressure exerted by the filling bag and thus with the known volume of the bag, this measurement is reported as the volume of bag content; and c) Level measuring sensors can be placed at defined vertical locations on the bag such that capacitance sensors, ultrasonic sensors or a microwave propagation phase shift sensors can measure the liquid and solid level of the bag as it fills.

Turbidity:

a) IT optical backscattering sensors having an embedded small IR LED in the parameter sensor with photodiodes surrounding the IR LED to measure the backscattering of the IR light from the particles in the bag with which the IR light interacts. Such measurements can provide the size of the particles and report on the turbidity (and thus consistency) of the contents; and b) Ultrasonic sensors (such as Doppler sensors) can be used as an alternative to the IR optical backscattering, the ultrasonic sensors can also be used to measure the contents and consistency of the stoma effluent in the bag.

Odor-Olfaction:

Nanosensor (or "e-nose") circuits can be used to measure a variety of odors, for example a methane and ammonia sensor can report any odors or leakages within the immediate environment of the parameter sensor.

Temperature:

A differential temperature sensor can be used to record changes in the temperature of the bag and/or the stoma effluent or bag contents.

Liquid Flow:

A flow sensor can be placed at the top of the bag and/or at the opening of the bag proximal its attachment to the stoma to measure all stoma effluent flow into the bag.

Leakage:

A parameter sensor that uses ink jet electrodes printed on paper can be used to measure leakage. The sensor paper is placed at the site of bag attachment to the stoma with the sensor paper surrounding the stoma or attached to the flange.

As the paper gets wet, from leakage, the electrodes changes resistance and report this to the communicator 730.

Analyte Sensor:

An analyte sensor can be used to measure the concentration of a component (in clinical chemistry), or chemical that is of interest. Examples of such analytes may be hydrogen sulfide, hydrogen, ethanol or methane. Sensor circuits can be used to measure a variety of analytes. The sensors may either be embedded in the bag facing the bag contents or they be on the external surface of the bag.

Activity:

A tri-axis or multi-axis accelerometer chip may be embedded on a circuit board within the measurement communicator 730 of the sensor device to report on movement and activity. The measurement communicator is configured to receive data from the accelerometer chip. Using the data, the direction/orientation of the patient's body can be calculated. This facilitates the determination of whether the patient is walking, lying down, sitting up with his body in an upright position, or leaning forward or any other direction. This information can be used to evaluate the fluid level measurements.

In one embodiment, the parameter sensor is a soft, ultra-sensitive wireless stretch sensor. In another embodiment, the parameter sensor may be a capacitive sensor. Capacitive sensors may be used to detect and measure fluid levels in the bag 700. In yet another embodiment, one parameter sensor 710 may be for detecting leakage, one parameter sensor 712 may be for turbidity, one parameter sensor 714 may be for temperature, and one parameter sensor 716 may be to report specific movements.

In one embodiment, as the bag 700 fills up, the parameter sensor 712 and/or 714 can measure, through the resistance of the strip, the bending and stretching of the bag. In yet another embodiment, the parameter sensor is a capacitive fluid sensor. Capacitive fluid sensors can measure the change in capacitance as the fluid levels rise. This embodiment can include two electrodes in a circuit or an array of sensors running vertically up and down the bag to measure increasing volume levels, as for example sensors 710,712, 714,716. The capacitance between the two electrodes is different when there is air (a non conducting medium of low dipole), versus fluid (having a higher dielectric constant). Therefore, as measurements are taken at predetermined set time intervals the fluid level rises and the bag fills up. In this case the fluid would have slightly different dielectric properties than water since it is urine and waste and there will be a detectable change along the many electrodes that would measure specifically where the fluid is in the bag.

Measurement Communicator.

Every parameter sensor must communicate the data gathered by the parameter sensor to a measurement communicator 730 where it is gathered, identified with a particular parameter sensor device and typically processed before being further communicated to the structural database 210 or the platform 150. The sensor device 750 includes at least one parameter sensor, at least one data processor, and at least one measurement communicator 730 that stores and transmits each measurement of the parameter being measured by the parameter sensor.

In one embodiment of the sensor device 750 a single parameter sensor is in communication with a single measurement communicator 730. In other embodiments, multiple parameter sensors are in communication with a single measurement communicator. For example, one embodiment shown in FIG. 8 has two parallel arrays 640 and 645 where each array has multiple parameter sensors of a single type.

Figure 8:
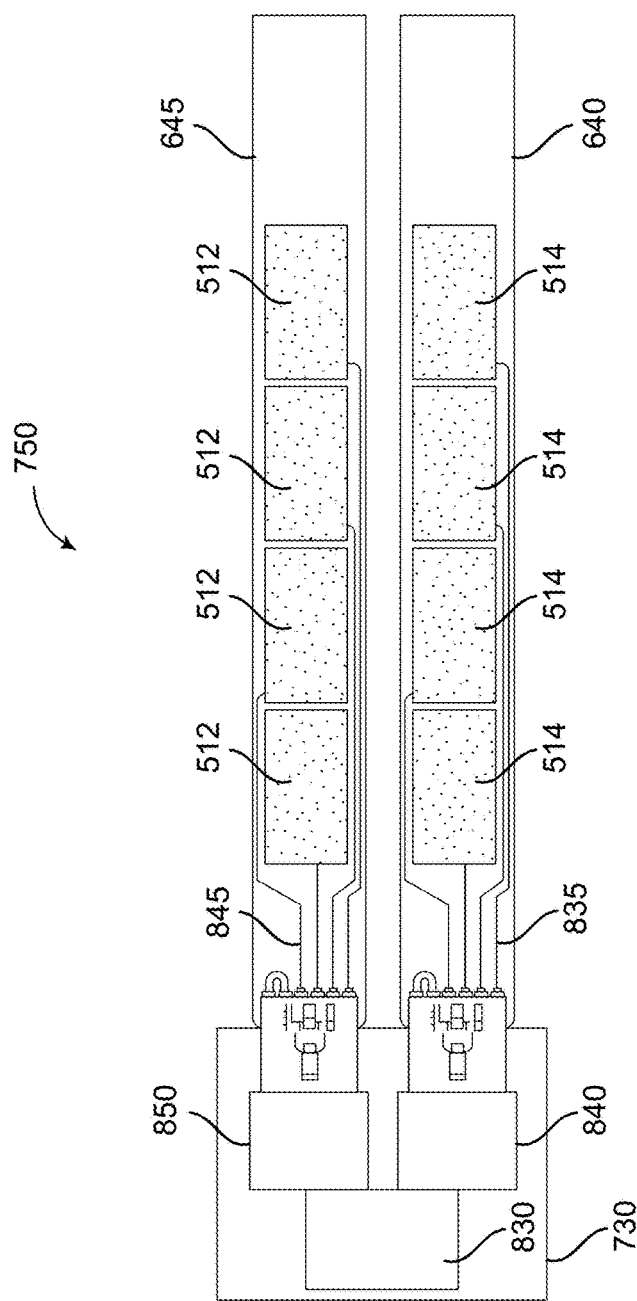
FIG. 8 is an illustration of a sensor device with two parameter sensor arrays connected to data processors and a measurement communicator.

Sensor array 640 has several parameter sensors 514, whereas sensor array 645 has several parameter sensors 512. Each sensor in each array must communicate with a data processor and a measurement communicator 730. The embodiment shown in FIG. 8 shows that each sensor 514 in the sensor array 640 communicates with a data processor 840 through a communication conduit 883, while each sensor 512 in the sensor array 645 communicates with a data processor 850 through a communication conduit 845. The data processors 840 and 850 may be the same or different and the communication conduits 835 and 845 may be the same or different. For example, the communication conduits 835 and 840 may both be wire connections or communication conduit 835 may be wire connections and communication conduit 845 may be optical fibers.

Figure 7B:
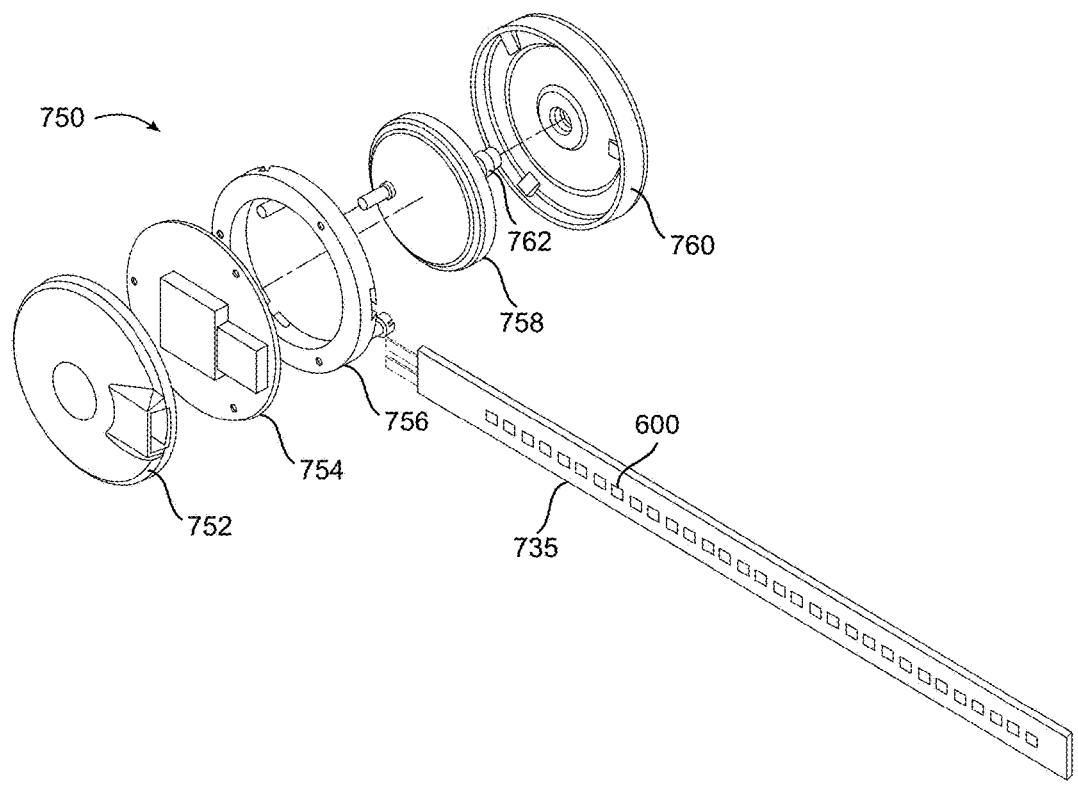
FIG. 7B is an exploded view of a sensor device according to an embodiment.

FIG. 7B is an exploded view of one embodiment a sensor device 750. The measurement communicator 730 has an upper 760 and a lower 752 end cap that are fitted together to enclose a data processor having a control board 754 such as a PCU (Programmable Control Unit) or a PCB (Printed Circuit Board), a battery retainer 756, and a battery 758. The mounting device 735 has an array of parameter sensors 600. In addition, the sensor device 750 may optionally have a parameter sensor such as an odor sensor that protrudes through the upper end cap. Each parameter sensor communicates with the data processor or control board that collects, identifies and processes each measurement from each parameter sensor and the broadcasts the measurement through the measurement communicator to the mobile application 180. Typically, the processing unit 120 and/or the data processor 150 receives the measurement signal from a parameter sensor 600, reformats the raw measurement signal and adds an identifier such as the time of the measurement and/or the identity of the specific parameter sensor that took the measurement.

The measurement communicator 730 is designed such that when the mounting device 735 is assembled with the measurement communicator that the parameter sensors mounted on the mounting device or embedded within the bag are in communication with the control board 754. Whenever an odor sensor, or any other sensor, is included in the sensor device, that parameter sensor must also have a communication conduit aligned to allow communication between the parameter sensor and the control board.

Stoma Care Management Software Application.

According to an embodiment, measurement data such as fill level measurement data from the bag 700 is periodically transmitted to a stoma care management software application. The stoma care management software application or mobile application may be configured to run on any portable or mobile device 180. The stoma care management software application may be available for download through app stores or distribution platforms. The mobile device 180 may include a smart phone or a tablet computer. The stoma care management software application includes computer program instructions for receiving the measurement data from the measurement communicator 730 via the data processor. The measurement data is transmitted from the data processor in binary format. The stoma care management software application includes computer program instructions for converting the transmitted data into a suitable format (for example, hexadecimal format). The stoma care management software application further includes computer program instructions for interpreting the formatted measurement data using a dictionary application. The stoma care management software application further includes computer program instructions to present a visual representation of the fill levels of the ostomy bag 700. One embodiment of the visual representation seen in FIG. 9 may be displayed on a display screen of the mobile device 180.

The measurement data is transmitted from the measurement communicator 730 to the platform 150 or mobile device 180 wirelessly through passive RFID, or a low energy Bluetooth radio or a GSM radio transmission, or direct transmission through the network to a server using wireless networks (a GSM or CDMA mobile system). typically, the formatted measurement data is transmitted to a platform 150 where it is analyzed and intervention triggers are activated as required.

By way of example and not limitation, the stoma care management software application running on a mobile device periodically receives measurements from the software application via the data processor and the measurement communicator on the fill levels of the collection bag. The measurements are interpreted by the stoma care management software application and the data is transferred to an interactive platform 150. The platform includes a knowledge module that is further configured to analyze the data received from the stoma care management software application and transfer the results of the analysis to a server 305 or portal 310 for stoma care management. The portal 310 includes a client sub-portal 310D that is configured to provide real-time personalized communications 360 giving appropriate warnings and alerts to the stoma patient or client. The client sub-portal 310D can be configured to deliver personalized care solutions for a stoma patient using information from a number of devices (including the aforementioned sensor device 750 and measurement communicator 730).

As described earlier, the measurement communicator 730 is configured to transmit stored effluent/fluid measurement data to a mobile device. This enables a patient to conveniently access information on the fluid levels in the collection bag. As shown in FIG. 7A, a mounting device 735 is attached to an ostomy bag 700. The mounting device 735 may includes a plurality of fluid sensors. A measurement communicator 730 is configured to receive and transmit data from the fluid sensors.

For example, four sensors 710,712,714 and 716 may be fluid sensors that are disposed along the length of the mounting device 735. The sensors 710,712,714 and 716 measure four levels of fluid inside the bag. When the measurement communicator 730 is powered, it goes into an advertising mode and looks for a suitable mobile device to pair with. A predetermined communication method, for example, Wi-Fi or a Bluetooth Low Energy (BLE) protocol can be used to achieve communication between the measurement communicator 730 and a suitable mobile device 180. The mobile device can be mobile phone or a PC. The mobile device is configured to receive data notifications from the measurement communicator 730. The mobile device 180 can be configured with or download a customizable dictionary application. In one or more embodiments, the manufacturer of the sensor device 750 can provide the dictionary. The dictionary is used to define the values and read the parameter data transmitted by measurement communicator 730. The measurement communicator can utilize the communication method of the mobile device 180.

After the connection is made, the measurement communicator 730 can start sending data notifications periodically to the mobile device. For example, the measurement communicator 730 can send data notifications every 10 minutes. The data format may be binary. The data can include measurements of one or more parameters, such as, fluid level data (gathered from the fluid sensors) and the X, Y and Z orientation of the patient (gathered from an accelerometer). The data may be transmitted with a predefined delay. For example, the delay may be less than 100 milliseconds. The measurement communicator 730 sends this data out as a notification and controls the frequency of broadcasts.

The mounting device 735 can be characterized by a unique identifier. When the sensor device 750 is connected to the mounting device 735, it reads the identifier and recognizes the mounting device 735. This data is also transmitted to the mobile device with the rest of the data. Each bag 700 can be identified uniquely because the mounting device 735 is attached to the bag 700. Therefore, when the patient changes the bag 700, the change can be easily tracked.

The data transmitted to and saved on the mobile device further includes the time stamp of each measurement. The time stamp serves as a unique identifier for each measurement. The time interval between two measurements is predefined. As such, this time stamp enables the calculation of how many measurements did not reach the mobile device.

The measurement communicator 730 can also calculate the rate of filling of the bag 700 for each patient. This calculation can be used to extract each patient's pattern of bag filling and therefore make a prediction of when the current bag will be filled up and alert the patient to any abnormalities. The data saved on the mobile device also includes the measurement of the detected parameter (for example, fluid level in the bag and/or the measurement of the accelerometer).

Figure 9:
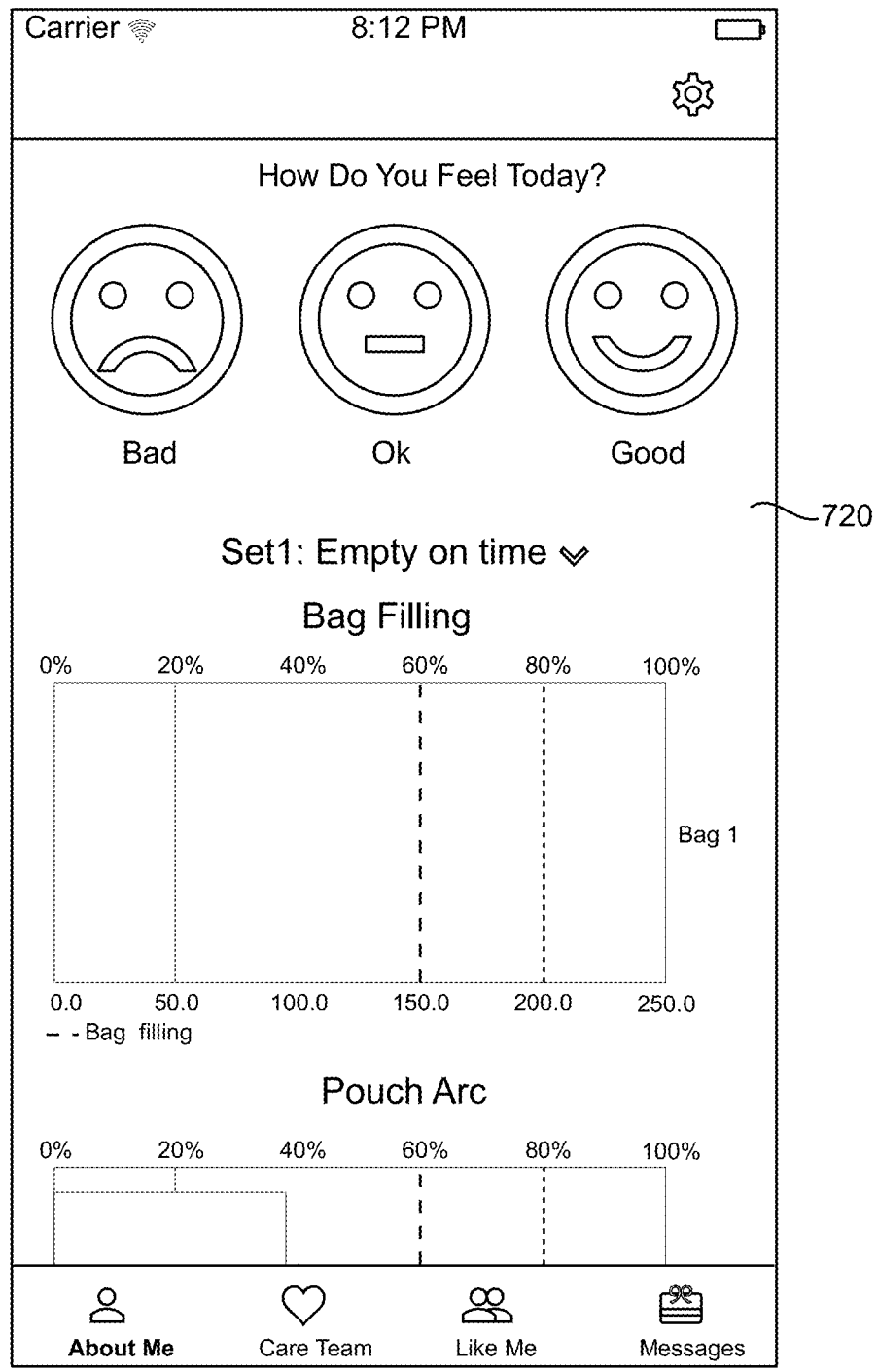
FIG. 9 is an exemplary display screen of a stoma care management software application according to an embodiment.

As shown in FIG. 9, the measurement of fluid levels can be visually represented on the mobile device. The measurement can be dynamically refreshed whenever there is a change in fluid levels. The fluid level visual representation provides the patient with an instant feedback mechanism about his bag filling. The fill rate can also be shown along with an estimate of when the bag needs to be changed. As shown in FIG. 9, a value can be sent from the measurement communicator 730 to the mobile device 720 to indicate the fill level of the bag 700. For example, as shown in FIG. 7A, since the bag is empty a corresponding code in binary format is transmitted to the mobile device 720. After the measurement is received by the mobile device, it is read in hexadecimal format and compared against the values provided in the dictionary to determine that the bag 700 is empty, partially filled or full.

In another embodiment (not shown), the measurement communicator is configured to receive data from an accelerometer. Using the data, the direction/orientation of the patient's body can be calculated. This facilitates the determination of whether the patient is lying down, sitting up with his body in an upright position, is leaning forward or any other direction. This information can be used to evaluate the fluid level measurements. For example, if there is a sudden rise in fluid level, the accelerator's measurements can be used to identify the reason for the same. If the accelerometer's measurements indicate that the increased fluid level occurred when the patient was leaning forward, an alert may not be raised. Otherwise, if the accelerometer's measurement indicates that the patient had his body in a straight or upright position, then the interpretation is that a medical reason may have caused the sudden rise in fluid levels. This results in an alert being transmitted to the mobile device to inform the patient of his condition. After sending the data packet, the measurement communicator 730 goes into a deep sleep mode for a set time period to conserve battery power.

Method for Providing Comprehensive Care

Figure 10:
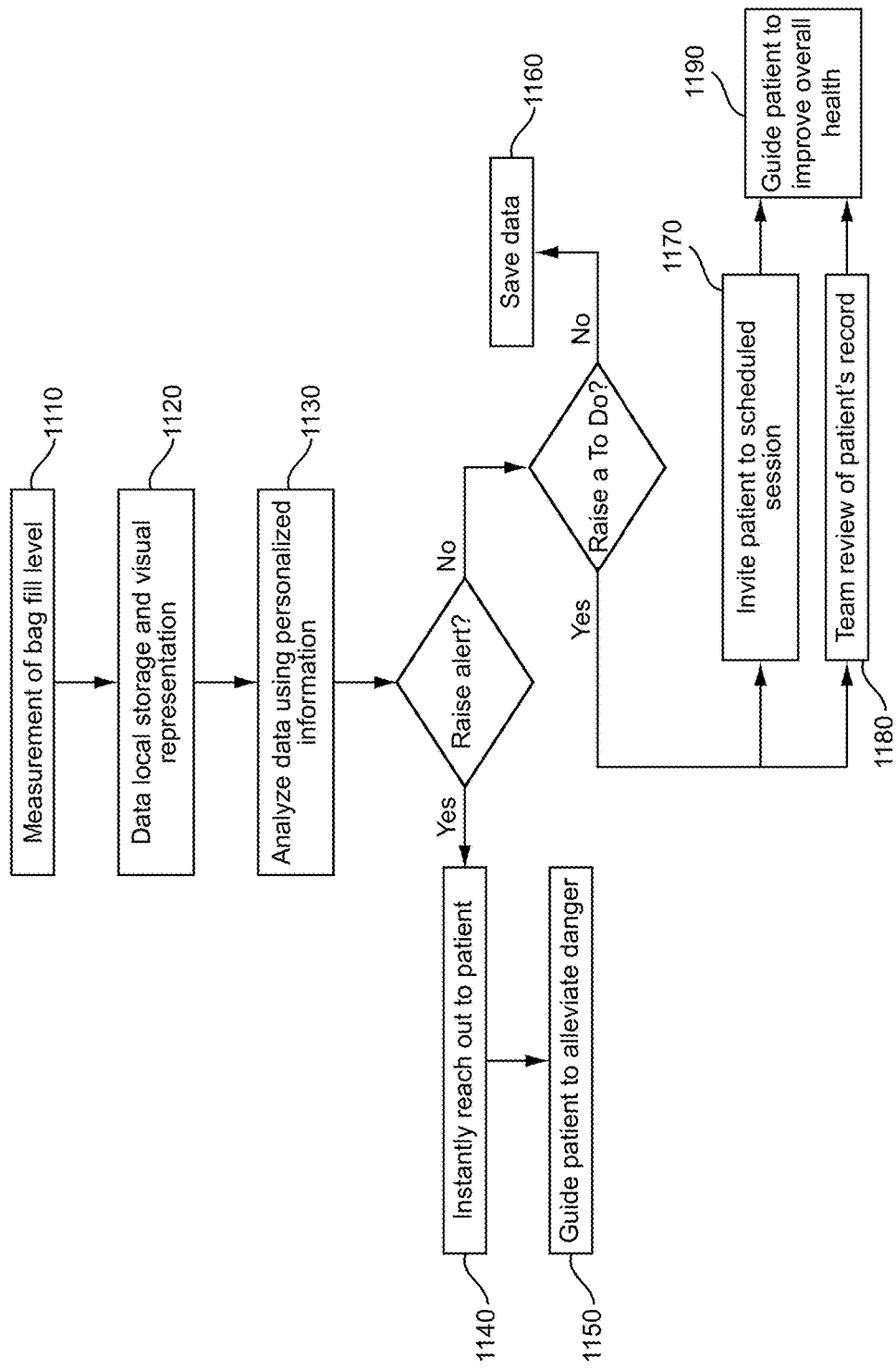
FIG. 10 is an illustration of a method for providing care to a stoma patient according to an embodiment.

An exemplary embodiment for a method of providing comprehensive care to a stoma patient is illustrated in FIG. 10. As shown, the method involves measuring the effluent (or any other parameter) levels in a collection bag to determine bag fill levels 1110. The fill levels can be measured at predetermined time intervals. For example, the fill levels can be measured every 250 milliseconds. an exemplary embodiment, effluent levels may be measured to determine 0%, 25%, 50%, 75% and 100% fill information. The measurements can be communicated to a mobile device using a wireless communication method.

As described earlier, the mobile device may be provided with an application that includes a dictionary to convert the transmitted measurement into hexadecimal values. These values are compared against the values provided in the dictionary to determine fill levels of the bag. The application further provides a visual representation of one or more parameters 1120. The visual representation may include color coded information, graphs, charts or icons on the level measurements, rate of filling up, number of bag changes and number of bags emptied and reused. The visual representation of the measured parameters allows the patients to quickly and easily decipher fill levels.

The measurements are transmitted to a knowledge module where they are analyzed in real-time 1130. The measurements are compared with the patient's records stored in a database. If the measurements are equal to or greater than a predetermined critical value, an alert is raised 1140. An alert is typically raised when the patient is suffering from a potentially life-threatening condition. Any alert mechanism known in the art can be used to notify the patient. For example, a text message can be sent to the user to contact a caregiver. The patient can then be guided to alleviate the potentially dangerous symptoms that caused the discrepancy in the measurements 1150. Even if the measurements do not warrant the raising of an alert, they may be analyzed to determine whether they raise a "To Do" or warning signal. A warning signal may be raised if the measurements are not equal to or greater than predetermined critical value but are within a predefined warning threshold. If a warning signal is also not warranted, the measurements are saved to the patient profile for future reference 1160. However, if a warning signal is raised, the patient may be invited to schedule a session with his Sherpa or caregiver 1170 and then guided to improve his overall health by making required adjustments to their diet, exercise, posture, etc. 1190. Alternately, a team of experts reviews the patient's records 1180 and guides the patient to improve his overall health 1190.

According to another embodiment, a method for determining the effect of diet, medication and activity on the bag fill rate is disclosed. This involves creating a plot of fill rate of the collection bag over a specified period. This further involves: (i) determining how increases or decreases in the certain foods (vegetables, meats, dairy, fish or seafood, fruits, etc.) correlate with increases or decreases in fill rate; (ii) correlating increases or decreases in fluids, including water, fruit juice, carbonated beverages, alcohol, and caffeine, with fill rate; (iii) determining if any particular combinations of foods or fluids cause increases or decreases in fill rate; (iv) correlating use of medications or supplements with fill rate; and (v) determining how increases or decreases in activity correlate with increases or decreases in fill rate. In one embodiment, the individual BMR and BMI may be determined to find the bag fill rates and to compile a set of warning messages to be transmitted to the patient. After the results are tabulated, a patient is provided with education and information, in real time, on managing their diet, medication and activity levels.

Because each individual's unique diet, activity level and physiology (including Body Mass Index and Basal Metabolic Rate) can affect the fill rate and fill levels, a further preferred embodiment involves compiling, at the user portal, the user diet, activity and fill rate information over time, and then establishing projected individual fill rates based on such information (and other known personal information such as BMI and BMR). The projected fill rate is continuously updated over time as data is accumulated. The updating is needed as the projected fill rate is expected to change over time with a user's changing physiology. As a database of projected individual fill rates grows, it allows a more accurate prediction of fill rates for new patients, for whom there is no prior fill rate information. Thus, increased reliability of projected fill rates for new patients is a significant benefit of one preferred embodiment.

In another aspect, the invention relates to uniquely tailored advice and recommendations, particular on diet, based on patient preferences. The advice and recommendations are continually updated and further refined as new information on preferences is added by the user. The individual tailoring of recommendations and advice is performed in view of the user's preferences, limitations and individualized risk assessment as continually updated.

The system may include algorithms that can sort through patient preferences for diet and exercise to provide uniquely tailored advice, recommendations and education for the patient. The number of selections by the algorithm quickly increases as the patient continues to provide feedback, leaving a set of instructions which is so detailed as to essentially be a unique code for the patient.

A procedure is here, and generally, conceived to be a sequence of steps leading to a desired result. These steps are those requiring physical manipulations of physical quantities. Usually, though not necessarily, these quantities take the form of electrical or magnetic signals capable of being stored, transferred, combined, compared, and otherwise manipulated. It proves convenient at times, principally for reasons of common usage, to refer to these signals as bits, values, elements, symbols, characters, terms, numbers, objects, attributes or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; various operations described herein may be automatic machine operations. Useful machines for performing the operations of the present invention include general purpose digital computers or similar devices.

Selected steps of the method may be executed on a general computer, such as a mainframe computer, personal computer or the like and pursuant to one or more, or a part of one or more, program modules or objects generated from any programming language, such as C++, Java, Fortran or the like. And still further, a step, or a file or object or the like implementing a step, may be executed by special purpose hardware or a circuit module designed for that purpose.

Aspects of the invention are implemented (in one example) in a high level procedural or object-oriented programming language to communicate with a computer. However, the inventive aspects can be implemented in assembly or machine language, if desired. In any case, the language may be a compiled or interpreted language.

The invention may be implemented as a mechanism or a computer program product comprising a recording medium. Such a mechanism or computer program product may include, but is not limited to CD-ROMs, diskettes, tapes, hard drives, computer RAM or ROM and/or the electronic, magnetic, optical, biological or other similar embodiment of the program. Indeed, the mechanism or computer program product may include any solid or fluid transmission medium, magnetic or optical, or the like, for storing or transmitting signals readable by a machine for controlling the operation of a general or special purpose programmable computer according to the method of the invention.

The procedures presented herein are not inherently related to a particular computing environment. The required structure for a variety of these systems will appear from the description given. Again, the capabilities of one or more aspects of the present invention can be implemented in software, firmware, hardware or some combination thereof.

One or more aspects of the present invention can be included in an article of manufacture (e.g., one or more computer program products) having, for instance, computer usable media. The media has therein, for instance, computer readable program code means or logic (e.g., instructions, code, commands, etc.) to provide and facilitate the capabilities of the present invention. The article of manufacture can be included as a part of a computer system or sold separately.

Additionally, at least one program storage device readable by a machine embodying at least one program of instructions executable by the machine to perform the capabilities of the present invention can be provided.

The flow diagram depicted herein is just an example. There may be many variations to the diagram or the steps (or operations) described therein without departing from the spirit of the invention. For instance, the steps may be performed in a differing order, or steps may be added, deleted or modified. All of these variations are considered a part of the claimed invention.

The specific systems and methods described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. The invention has been described broadly and generically herein.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A care management system including:
   a) an information management system for receiving and storing a structured database, an unstructured database, and an internet usage database for an individual participant in the care management system;
   b) an ostomy bag comprising: a) an attachment site that provides a fluid connection between an interior of the ostomy bag and a patient stoma; b) a sensor device having a mounting device that is attached to the ostomy bag via an attachment strip, wherein the mounting device comprising an array of multiple types of parameter sensors, wherein the array of multiple types of parameter sensors are configured to measure different parameters of a stoma effluent received in the ostomy bag, wherein the parameter sensors comprise level measuring sensors placed at different, defined, vertical locations on the bag, the level measuring sensors configured to measure the liquid and solid level of the bag as it fills; and c) at least one measurement communicator attached to the ostomy bag, wherein the at least one measurement communicator has an upper end cap and a lower end cap that are fitted together to enclose a data processor, wherein the data processor is configured to: (i) receive a raw measurement signal from a parameter sensor from the array of multiple types of parameter sensors, (ii) reformat the raw measurement signal, (iii) add an identifier corresponding to the time of measurement and an identity of the specific parameter sensor that took the measurement, and to (iv) communicate the reformatted measurement signal along with the identifier to the structured database;
   c) a processing unit, wherein the processing unit comprises computer program instructions for extracting, analyzing and correlating information relevant to the designated health condition of the individual participant from the information management system and an external data source to form a searchable combined information system; and
   d) a wireless platform in communication with the processing unit and the searchable combined information system, wherein the platform comprises one or more portals, and wherein the platform is configured to maintain an interactive user database for an authorized user of the portal.

2. The care management system according to claim 1, further including a data repository in communication with the searchable combined information system and the platform.

3. The care management system according to claim 1, wherein the ostomy bag is in communication with the information management system and a mobile device.

4. The care management system according to claim 1, wherein the portal is configured to add contextual metadata to at least a subset of the searchable combined information system, wherein the contextual metadata comprises one or more tags that identifies an origin of the subset of the searchable combined information system within one or more sub-portals.

5. The care management system according to claim 4, wherein each sub-portal has restricted access for an authorized user.

6. The care management system according to claim 5, wherein each sub-portal is interactive with the authorized user.

7. The care management system according to claim 4, wherein one sub-portal is accessible by the individual participant on a wireless device.

8. The care management system according to claim 6, wherein one sub-portal is accessible by a caregiver assigned to the individual participant and wherein the caregiver sub-portal communicates with the individual participant sub-portal.

9. The care management system according to claim 1, wherein the platform is configured to send queries to the individual participant and to analyze the received information from the individual participant to provide reminders, advice and coaching to the individual participant.

10. The care management system according to claim 1, wherein the searchable combined information system includes information and data extracted from unstructured data provided by the individual participant and other care management system participants.

11. A care management system including:
a) an information management system for receiving and storing a structured database, an unstructured database, and an internet usage database for an individual participant of a care management system;
b) an ostomy bag comprising: a) an attachment site that provides a fluid connection between an interior of the ostomy bag and a patient stoma; b) a sensor device having a mounting device that is attached to the ostomy bag via an attachment strip, wherein the mounting device comprising an array of multiple types of parameter sensors, wherein the array of multiple types of parameter sensors are configured to measure different parameters of a stoma effluent received in the ostomy bag, wherein the parameter sensors comprise level measuring sensors placed at different, defined, vertical locations on the bag, the level measuring sensors configured to measure the liquid and solid level of the bag as it fills; and c) at least one measurement communicator attached to the ostomy bag, wherein the at least one measurement communicator has an upper end cap and a lower end cap that are fitted together to enclose a data processor, wherein the data processor is configured to: (i) receive a raw measurement signal from a parameter sensor from the array of multiple types of parameter sensors, (ii) reformat the raw measurement signal, (iii) add an identifier corresponding to the time of measurement and an identity of the specific parameter sensor that took the measurement, and to (iv) communicate the reformatted measurement signal along with the identifier to the structured database;
c) a processing unit storing a plurality of software applications including a data extraction application that identifies and links associated processed data from the structured database, the unstructured database, the internet usage database, and an external data source and a data analysis application that analyzes and correlates the linked information relevant to a designated health condition of the individual participant; and
d) a platform in communication with the processing unit and one or more portals, wherein the platform is configured to maintain an interactive participant database accessible by an authorized user of the portal, wherein the portal is configured to append contextual metadata to at least a subset of data communicated to the platform, the contextual metadata including one or more metatags that identifies an origin of the subset of data within one or more sub-portals.

12. The system according to claim 11, wherein the contextual metadata further comprises at least an unique identifier associated with access privileges for a particular sub-portal.

13. The care management system according to claim 11, wherein the platform is configured to send queries to the individual participant and to analyze the received information from the individual participant to provide reminders, advice and coaching to the individual participant.

14. The care management system according to claim 11, wherein the ostomy bag is in communication with the information management system and a mobile device.

* * * * *